United States Patent [19]
Silverman et al.

[11] Patent Number: 5,060,393
[45] Date of Patent: Oct. 29, 1991

[54] APPARATUS FOR TAKING BODY MEASUREMENTS

[75] Inventors: Michael W. Silverman, Highland Park; Michael Heinrich, Chicago, both of Ill.; C. Kerry Jones, South Bend, Ind.

[73] Assignee: Pin Dot Products, Niles, Ill.

[21] Appl. No.: 667,670

[22] Filed: Mar. 11, 1991

[51] Int. Cl.⁵ ............................................. A61B 5/10
[52] U.S. Cl. ...................................... 33/512; 33/515
[58] Field of Search ................. 33/511, 512, 515, 2 R, 33/15, 16; 128/774

[56] References Cited

U.S. PATENT DOCUMENTS

| | | | |
|---|---|---|---|
| 2,053,810 | 9/1936 | Bisel | 33/512 X |
| 3,196,551 | 7/1965 | Provost et al. | 33/515 |
| 4,525,130 | 6/1985 | Netznik | |
| 4,615,856 | 10/1986 | Silverman | |
| 4,728,150 | 3/1988 | Gaudreau | 33/515 X |

Primary Examiner—Harry N. Haroian
Attorney, Agent, or Firm—Emrich & Dithmar

[57] ABSTRACT

Apparatus for taking body measurements of a seated person for making individually sized seat and back support cushions includes a foldable frame having a first leg/buttocks rule and a second height rule pivotally coupled together and adapted for positioning adjacent the leg/buttocks and back portions, respectively, of a person positioned thereon. The height rule is moveable along the length of the leg/buttocks rule upon which the person being measured is seated for measuring the distance from the seated person's buttocks to his or her knees. A moveable, generally V-shaped bracket adapted for engaging the person's shoulders is attached to the height rule and allows the person's seat-to-shoulder dimension to be measured. A moveable third rule attached to the leg/buttocks rule and disposed between its knee engaging end and the height rule includes a pair of moveable hip engaging paddles for measuring the person's hip width. A fourth rule movably attached to the second height rule also includes a pair of moveable torso engaging paddles for measuring torso width. Detents disposed along each of the rules at regular, spaced intervals are adapted to receive and maintain in position the height rule, the V-shaped bracket and the hip and torso rules for accurate measurement of the various dimensions. The foldable frame and the sliding, removable engagement of the several paddles of the hip and torso rules permit easy disassembly and folding of the apparatus into a compact configuration when not in use.

23 Claims, 2 Drawing Sheets

APPARATUS FOR TAKING BODY MEASUREMENTS

FIELD OF THE INVENTION

The present invention relates generally to apparatus for measuring various dimensions of the human body and is particularly directed to an arrangement for taking body measurements of a person while seated.

BACKGROUND OF THE INVENTION

Seat and back support cushions having contoured support surfaces are highly desirable for various reasons. For example, seating surfaces contoured and dimensioned for the individual user allow for a more uniform spreading over the entire seating surface of the user's weight for increased comfort. In the case of a wheelchair-bound user, the added comfort of a contoured seating surface is evidenced in substantially reduced likelihood of the formation of pressure sores. Contoured seating surfaces also may provide lateral support which may be particularly important for the infirm or handicapped.

The prior art includes various approaches for fabricating individually contoured seat and back support cushions. U.S. Pat. Nos. 4,615,856, issued Oct. 7, 1986, and 4,525,130, issued June 25, 1985, disclose apparatus for forming an individually contoured seat such as for a wheelchair employing flexible, sealed, bead-filled seat and back bags which are evacuated while the person being fitted is seated thereon to form a fixed impression of the person's support surfaces. Positive molds of the individual's support surfaces are then made, with the positive mold impression then utilized in cooperation with a molding frame to mold custom-fitted seat and back cushions which are particularly adapted for mounting in a wheelchair.

It is frequently not necessary to provide support cushions which are custom contoured in accordance with the dimensions and configuration of the user. For example, where the intended user does not suffer from a deformity, a cushion contoured in accordance with standard dimensions and configurations may be equally suitable at a much reduced cost. The use of contoured support cushions having a range of standard sizes for wheelchair use in one of several standard contoured support surfaces are becoming increasingly popular. This is particularly true in the case of children who do not suffer from a degenerative condition. In this case, it is highly desirable to fit the child with a standard contoured support cushion which may be replaced with a larger cushion at reasonable cost as the child grows.

Although the standard contoured support cushion is becoming increasingly popular, difficulties in making accurate measurements for a proper fitting of the cushion remain. While there are techniques and devices available for accurately measuring the circumference of anatomical members, it is difficult to accurately measure linear dimensions of various body parts. This difficulty is primarily due to the non-linear nature of most body parts because surfaces along which measurements are taken are typically curved and somewhat irregular. A shoe gauge is an example of one device which has been used to take such measurements, but such devices are limited in application to measuring the relatively linear dimensions of the human foot. Accurately measuring the seating support dimensions of a person being fitted with a standard back or seat support cushion has therefore been a problem and frequently results in improper cushion fitting.

OBJECTS AND SUMMARY OF THE INVENTION

Accordingly, it is an object of the present invention to accurately measure various dimensions of a person in a seated position for the purpose of fabricating individually sized seat and back cushions.

It is another object of the present invention to provide apparatus for measuring one's seating dimensions which is easy to use, inexpensive, provides highly accurate and reliable measurements and can be folded to a compact configuration when not in use.

Yet another object of the present invention is to provide accurate measurements of one's knee-to-seat, shoulder-to-seat and hip and torso width dimensions while seated for fabricating individually sized seat and back support cushions.

A further object of the present invention is to allow for the fabrication of seat and back cushions which may be precisely sized and contoured over a wide range of intended user dimensions and configurations.

This invention contemplates apparatus for measuring the dimensions of a person in a seated position, the apparatus comprising: a first measuring rule for receiving a person seated thereon and for measuring the person's knee-to-buttocks dimension; a second measuring rule coupled to the first measuring rule and moveable along the length thereof, the second measuring rule adapted for positioning adjacent to the back of the seated person for measuring the person's shoulder-to-buttocks dimension; a third measuring rule coupled to the first measuring rule and moveable along the length thereof and adapted to engage opposed lateral hip portions of the person for measuring the width of the person's hips; and a fourth measuring rule coupled to the second measuring rule and moveable along the length thereof for measuring the width of the person's torso.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

DETAILED DESCRIPTION OF THE INVENTION

Figure 1:
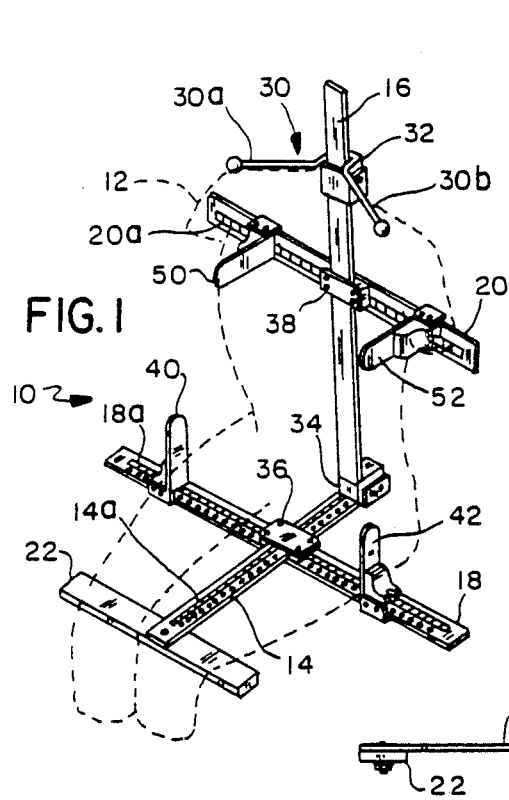
FIG. 1 is an upper perspective view of apparatus for taking body measurements in accordance with the present invention showing the outline of a human body in dotted line form positioned on the apparatus.

Referring to FIG. there is shown an upper perspective view of an apparatus for taking body measurements 10 in accordance with the present invention. Side and top plan views of the apparatus for taking body measurements 10 are respectively shown in FIGS. 2 and 3. The outline of the body of a person 10 positioned on the apparatus is shown in dotted line form.

The body measuring apparatus 10 includes a first, generally horizontally oriented rule 14 upon which the person 12 to be measured is positioned. The body measuring apparatus 10 further includes a second rule 16 pivotally coupled to the first rule 14 and adapted for generally vertical positioning adjacent to the back portion of the person 12. The second rule 16 is also adapted for sliding positioning along the length of the first rule 14 as described below. The first rule 14 includes a measurement scale 14a on its upper surface, while the second rule 16 also includes a measurement scale on its aft surface which is not shown in the figure. Each of the measurement scales extends substantially along the entire length of each of the first and second rules 14, 16. The first rule 14 is typically positioned on a flat surface such as that of a table when the body measuring apparatus 10 is being used.

Securely attached in a fixed manner to a front end of the first rule 14 is cross-member 22 which is adapted for positioning in tight fitting engagement with the aft knee portion, or popliteal area, of the person 12 being measured. The lower end of the second rule 16 is positioned adjacent to the buttocks of the person 12 to permit the second rule to extend upward along the back of the person being measured. The position of a sliding bracket 34 coupling the first and second rules 14, 16 on the scale of the first rule as measured from the cross-member 22 gives the dimension of the length of a seat cushion (not shown) fitted to the size of the person 12 being measured. Positioned in a sliding manner on the second rule 16 is a shoulder engaging member 30. The shoulder engaging member includes a sliding bracket 32 attached to the second rule 16 and first and second arms 30a and 30b. Each of the first and the second arms 30a, 30b is adapted for positioning upon a respective shoulder of the person 12 being measured. The position of the shoulder engaging member 30 on the measuring scale (not shown) on the aft surface of the second rule 16 provides a measure of the length of a back cushion for the person 12 being measured. The shoulder engaging member 30 is freely slidable along the length of and may be removed from the second rule 16.

Figure 2:
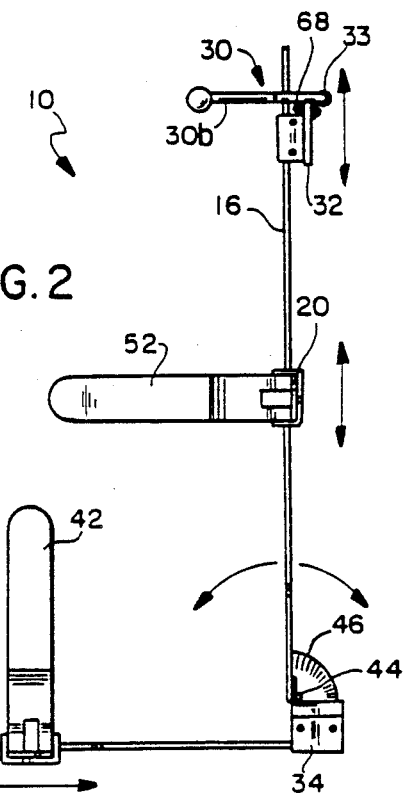
FIG. 2 is a side plan view of the apparatus for taking body measurements shown in FIG. 1.

As shown in FIG. 2, when the body measuring apparatus 10 is unfolded to the use configuration, the arms (only one of which arms 30b is shown in the figure for simplicity) of the shoulder engaging member 30 are arranged in a generally horizontal orientation. The arms of the shoulder engaging member 30 are maintained in this horizontal orientation during use while engaging the shoulders of the person being measured by means of a cross pin 68 inserted through sliding bracket 32 and upon which the arms of the shoulder engaging member 30 rest. The arms 30a, 30b of the shoulder engaging member 30 are pivotally coupled to sliding bracket 32 by means of a pivot bracket 33.

The body measuring apparatus 10 further includes a third rule 18 coupled to the first rule 14 by means of a sliding bracket 36 described in detail below. The third rule 18 and sliding bracket 36 combination can be slid along the length of the first rule 14. Positioned on opposed portions of the third rule 18 and on opposite sides of the first rule 14 are first and second paddles 40 and 42. The first and second paddles 40, 42 are slidable along the length of the third rule 18 and are adapted for engaging opposed, lateral hip portions of the person 12 being measured. The positions of the first and second paddles 40, 42 along the scale of the third rule 18 indicate the width of the person 12 being measured such as at the location of his or her greater trochanter. As shown in the figures, a preferred embodiment of the third rule 18 is provided with a pair of scales 18a and 18b on respective sides of the first rule 14 which not only allow hip width to be measured, but also permit any asymmetry to be detected and measured. The position of sliding bracket 36 coupled to the third rule 18 along the length of the scale on the first rule 14 indicates the location of the widest dimension of a person's hips along the person's knee-to-backside dimension. Measurements made with the third rule 18 are useful in determining seat cushion width.

Coupled to the second rule 16 in a sliding manner by means of a bracket 38 is a fourth rule 20. The fourth rule 20 includes a pair of spaced measuring scales on its forward surface as well as third and fourth paddles 50 and 52. The third and fourth paddles 50, 52 are positioned on opposed portions of the fourth rule 20 in a sliding manner and are on opposite sides of the second rule 16. Each of the third and fourth paddles 50, 52 is adapted for engagement with a lateral portion of the torso of the person 12 being measured such as at the location of his or her axilla, or arm pits. The positions of the third and fourth paddles 50, 52 on the scales of the fourth rule 20 provide a measure of the width as well as the symmetry of the person's torso. The position of sliding bracket 38 coupled to the fourth rule 20 along the length of the measuring scale (not shown) on the aft surface of the second rule 16 provides a measure of the height of the positions of the third and fourth paddles 50, 52. This measurement is useful in determining the height of lateral support contours in the back cushion. In a preferred embodiment, each of the paddles 40, 42, 50 and 52 as well as the cross-member 22 is comprised of wood, while each of the rules 14, 16, 18 and 20 is comprised of a metal such as aluminum or of a hard plastic such as Delron. Measurements made with the fourth rule 20 are useful in determining back cushion width.

As shown in FIG. 2, the second rule 16 is coupled to sliding bracket 34 by means of a hinge 44. Hinge 44 allows forward and aft pivoting displacement of the second rule 16 relative to the first rule 14, depending upon the orientation of the back of the person being measured relative to his or her buttocks positioned upon the first rule.

Figure 4:
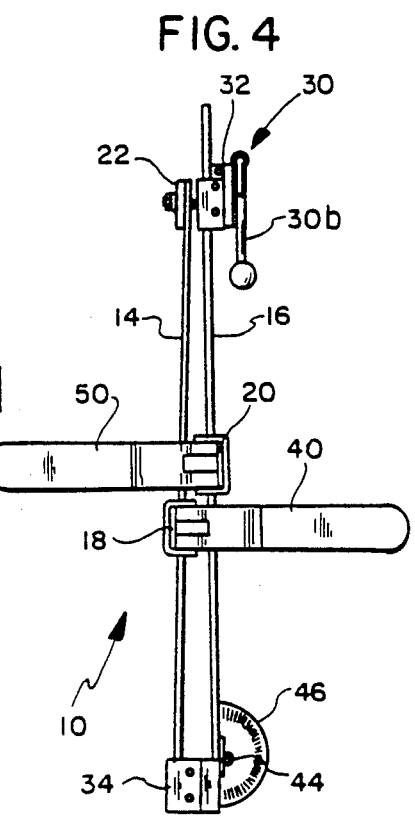
FIG. 4 is a side plan view of the apparatus for taking body measurements of the present invention shown in the folded configuration.

FIG. 4 is a side view of the body measuring apparatus 10 shown in the fully folded configuration. In this configuration, the first and second rules 14, 16 are folded toward one another by means of hinge 44 and are arranged in a closely spaced configuration. Although the paddles 40 and 50 are shown positioned respectively on the first and second rules 14, 16 when the body measuring apparatus 10 is folded, each of the paddles is adapted for sliding removal from its associated rule to further reduce the size of the apparatus when folded. The first and second arms 30a, 30b are pivotally coupled to sliding bracket 32 and assume an alignment generally parallel to the folded first and second rules 14, 16 when the apparatus 10 is folded.

Figure 5A:
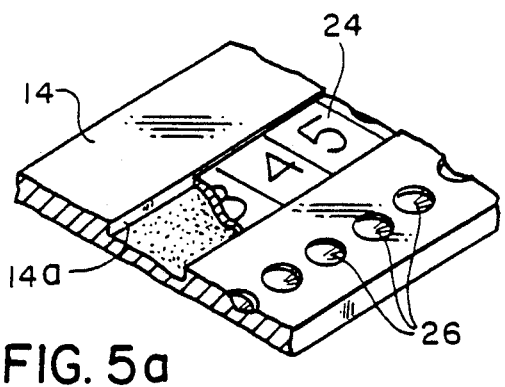
FIGS. 5a, 5b and 5c illustrate details of a rule and measuring scale thereon as used in the apparatus for taking body measurements of the present invention.
Figure 5B:
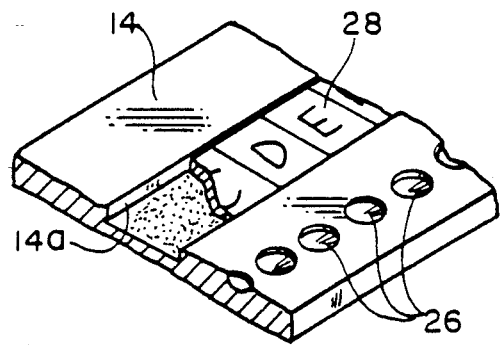
Figure 5C:
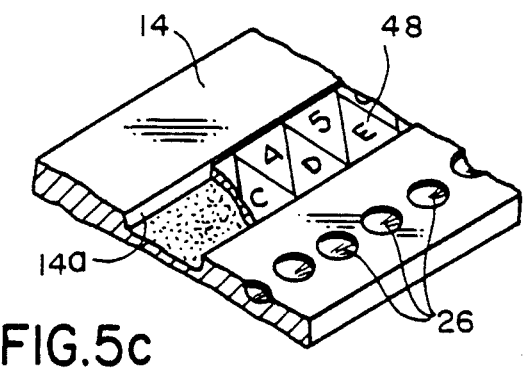

Referring to FIGS. 5a, 5b and 5c, there is shown an example of a first rule 14 having three different scales for measuring the dimensions of a person positioned upon the body measuring apparatus. Although the following discussion is directed to the scales used on the first rule 14, it is equally applicable to the second, third and fourth rules 16, 18 and 20 used in the body measuring apparatus. As shown in the figures, the first rule 14 includes an elongated, linear slot, or cutout portion, 14a extending substantially along the entire length thereof. Positioned within the slot 14a in the first rule 14 is a numerical scale 24 for the case shown in FIG. 5a. FIG. 5b shows the first rule 14 provided with a letter scale 28 which makes use of the alphabetical ordering of letters for providing the person's dimensions. Finally, the arrangement shown in FIG. 5c includes a composite scale 48 on the first rule 14. The composite scale 48 shown in FIG. 5c makes use of a combination of letters and numbers for indicating a measured dimension of a person positioned on the body measuring apparatus. A composite scale 48 may be desirable in making measurements for different groups of people having different dimensional characteristics such as men and women. Thus, the numbers in the composite scale 48 may be used to designate male measurements, while the letters may be used to designate female measurements. By designating the measurements either male or female other characteristics of the cushions dimensioned in accordance with the size of the person being measured may be taken into account. These other characteristics may include, but are not limited to, the thickness of the cushions, their depth of contour, etc. Rather than position the scale 24 in a slot 14a in the first rule 14, the scale may be embossed or applied to the surface of the rule.

As shown in FIGS. 5a, 5b and 5c, the first rule 14, as well as the other rules, includes a plurality of spaced recessed detents 26 along the length of the rule. Each of these detents 26 is adapted to receive an insert from either a slidable bracket or paddle as described in the following paragraphs.

Figure 6:
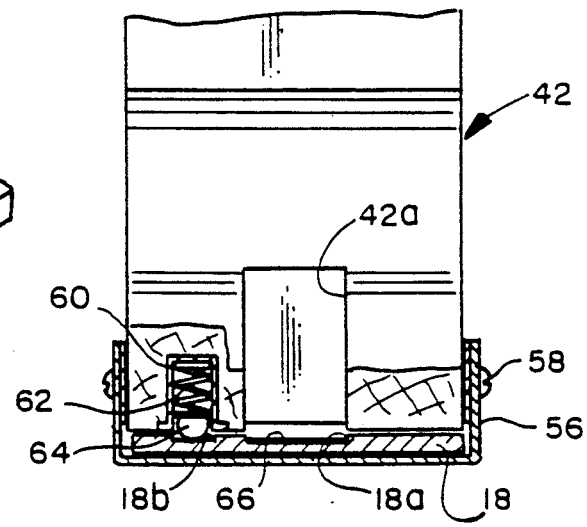
FIG. 6 is a sectional view of a portion of the body measuring apparatus of FIG. 1 taken along site line 6—6 showing details of a paddle positioned on a rule of the apparatus.

Referring to FIG. 6, there is shown a sectional view of the second paddle 42 positioned on the third rule 18. As shown in the figure, the third rule 18 is in intimate contact with the lower end portion of the second paddle 42. The third rule 18 includes an elongated, linear slot 18a extending substantially the length thereof and in which is positioned a scale 66. A lower lateral portion of the second paddle 42 is provided with a cutout/indicator notch 42a. The location of an edge of the cutout/indicator notch 42a along the length of the scale 66 provides an indication of the measured dimension of a person positioned upon the body measuring apparatus. Securely coupled to a lower end portion of the second paddle 42 by means of a plurality of connecting pins 58 is a generally U-shaped bracket 56. Rule 18 is positioned between the lower end portion of the second paddle 42 and a flat, intermediate portion of the U-shaped bracket 56 and is maintained in intimate contact with both the paddle and bracket. As described above and as shown in FIGS. 5a, 5b and 5c, each of the rules is provided with a plurality of spaced recessed detents one of which is shown as element 18b for rule 18 in the sectional view of FIG. 6. A lower end portion of the second paddle 42 is provided with a recessed portion, or notch, 60. Notch 60 is adapted to receive the combination of a coiled spring 62 and an insert member 64. Coiled spring 60 urges the insert member 64 downward and into the recessed detent 18b positioned in alignment with the bottom notch 60 of the second paddle 42. With the insert member 64 disposed within the recessed detent 18b, the second paddle 42 is securely maintained in position at the measured dimension on the third rule 18 to allow for accurate measurement of the person's dimensions. Downward biasing of the coiled spring 62 and positioning of the insert member 64 within the recessed detent 26 can be overcome by engaging and displacing paddle 42 along the length of the rule 18. Space is provided between the upper surface of the third rule 18 and a center portion on the bottom of the second paddle 42 to accommodate a surface mounted, or embossed, scale on the rule.

Figure 3:
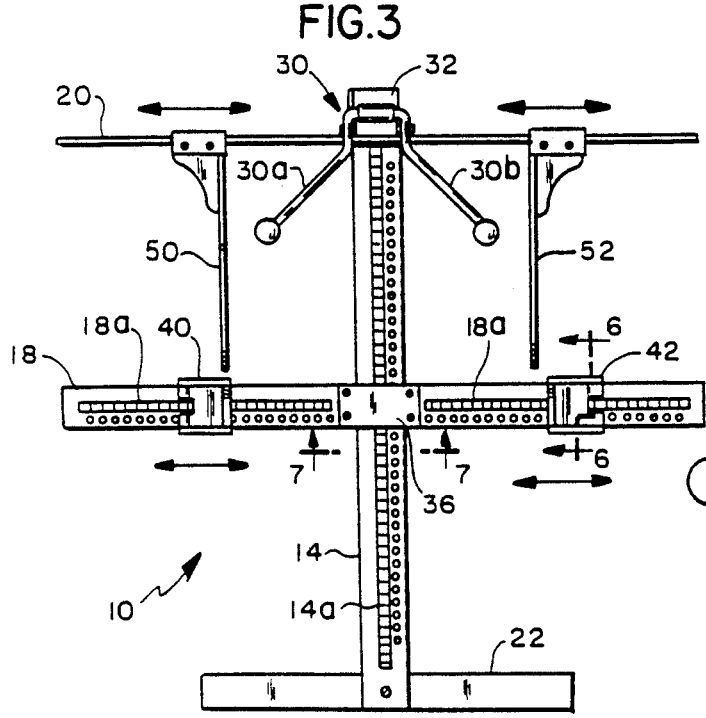
FIG. 3 is a top plan view of the apparatus for taking body measurements shown in FIG. 1.
Figure 7:
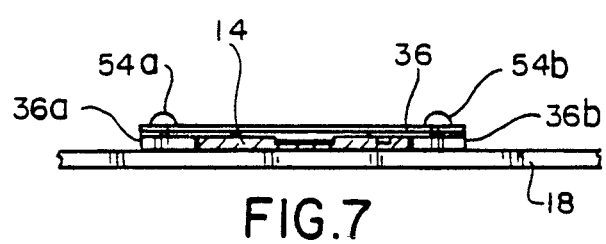
FIG. 7 is a sectional view of a portion of the body measuring apparatus of FIG. 1 taken along site line 7—7 therein showing details of the manner in which two rules are coupled together in a sliding manner.

Referring to FIG. 7, there is shown a sectional view of a portion of the body measuring apparatus 10 shown in FIG. 3 taken along site line 7—7 therein. In the view of FIG. 7, bracket 36 is shown securely coupled to the third rule 18 by means of a plurality of connecting pins 54b, such as rivets. A space within sliding bracket 36 is adapted for receiving the first rule 14 in allowing it to be displaced relative to the third rule 18 in a generally transverse direction. Spacers 36a and 36b within sliding bracket 36 allow for proper spacing in the bracket to receive the first rule 14.

There has thus been shown a body measuring apparatus for taking body measurements of one in a seated position. These measurements include the person's knee-to-buttocks, buttocks-to-shoulders and hip and torso width dimensions. The apparatus is also capable of measuring asymmetries in the person's body structure. The body measuring apparatus is inexpensive, easily used to make highly accurate and reliable measurements, and can be folded to a compact configuration when not in use.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. Apparatus for measuring the dimensions of a person in a seated position, said apparatus comprising:
   first measuring means for receiving a person seated thereon and for measuring the person's knee-to-buttocks dimension;
   second measuring means coupled to said first measuring means and moveable along the length thereof, said second measuring means adapted for positioning adjacent to the back of the seated person for measuring the person's shoulder-to-buttocks dimension;
   third measuring means coupled to said first measuring means and moveable along the length thereof and adapted to engage opposed lateral hip portions of the person for measuring the width of the person's hips; and fourth measuring means coupled to said second measuring means and moveable along the length thereof for measuring the width of the person's torso.

2. The apparatus of claim 1, wherein said first, second, third and fourth measuring means respectively include first, second, third and fourth elongated, linear rules each having a respective scale with units of measure thereon.

3. The apparatus of claim 2, wherein each of said rules further includes a plurality of spaced detents and wherein each of said detents corresponds with a unit of measure on the scale of its associated rule.

4. The apparatus of claim 3, wherein said units of measure are in inches.

5. The apparatus of claim 3, wherein said units of measure are indicated by a respective letter and said letters are arranged in alphabetical order.

6. The apparatus of claim 2 further comprising coupling means for pivotally coupling said first and second rules and allowing said first and second rules to be arranged in a folded configuration.

7. The apparatus of claim 6, wherein said coupling means further includes indicator means disposed adjacent to the scale on said first rule for indicating the person's knee-to-buttocks dimension.

8. The apparatus of claim 2, wherein said second rule includes an indicator moveable along the length thereof for engaging the person's shoulders and providing an indication of the person's shoulder-to-buttocks dimension.

9. The apparatus of claim 8, wherein said indicator includes a Y-shaped bracket for engaging both shoulders of the person being measured.

10. The apparatus of claim 9, wherein said indicator is disposed immediately adjacent to the scale on said second rule.

11. The apparatus of claim 2, wherein said third measuring means further includes first and second paddle means slidably attached to said third rule and moveable along the length thereof for engaging a person's opposed lateral hip portions.

12. The apparatus of claim 11, wherein each of said paddle means includes a respective indicator means disposed adjacent to the scale on said third rule for indicating the width of the person's hips.

13. The apparatus of claim 12, wherein each of said paddle means is comprised of wood.

14. The apparatus of claim 13, wherein each of said paddle means is removable from said third rule in a sliding manner.

15. The apparatus of claim 2, wherein said fourth measuring means includes third and fourth spaced paddle means slidably attached to said fourth rule and moveable along the length thereof for engaging opposed lateral portion of the person's torso.

16. The apparatus of claim 15, wherein each of said paddle means includes a respective indicator means disposed adjacent to the scale on said fourth rule for indicating the width of the person's torso.

17. The apparatus of claim 16, wherein each of said paddle means is comprised of wood and is positioned adjacent a respective axilla of the person being measured.

18. The apparatus of claim 17, wherein each of said paddle means is removable from said fourth rule in a sliding manner.

19. The apparatus of claim 2 further comprising a cross-member disposed on one end of said first rule for engaging an aft portion of the person's knees.

20. The apparatus of claim 19, wherein said cross-member is oriented generally transverse to said first rule and is comprised of wood.

21. The apparatus of claim 2, wherein each of said rules is comprised of metal.

22. The apparatus of claim 1 further comprising fifth measuring means for measuring the angle between said first and second measuring means.

23. Apparatus for measuring dimensions of a person seated thereon, said apparatus comprising:

a foldable frame including first and second rules pivotally coupled together and adapted for positioning adjacent to the buttocks and back of the person, respectively, for measuring the person's knee-to-buttocks and shoulder-to-buttocks dimensions, wherein said first rule includes a first end having a cross-member for engaging an aft portion of the person's knees and said second rule includes a moveable shoulder engaging member;

a third rule slidably coupled to said first rule and including a first pair of moveable paddles for engaging opposed lateral portions of the person's hips for measuring the width of the person's hips; and a fourth rule slidably coupled to said second rule and including a second pair of moveable paddles for engaging opposed lateral portions of the person's torso for measuring the width of the person's torso.

* * * * *

UNITED STATES PATENT AND TRADEMARK OFFICE
CERTIFICATE OF CORRECTION

PATENT NO. : 5,060,393

DATED : October 29, 1991

INVENTOR(S) : Michael W. Silverman et al.

It is certified that error appears in the above-identified patent and that said Letters Patent is hereby corrected as shown below:

Col. 3 / Line 8: After "FIG.", insert the number --1--.

Signed and Sealed this

Twenty-third Day of February, 1993

Attest:

STEPHEN G. KUNIN

Attesting Officer     Acting Commissioner of Patents and Trademarks